United States Patent
Bruder et al.

(10) Patent No.: US 11,826,673 B2
(45) Date of Patent: Nov. 28, 2023

(54) SOLVENT-LESS EXTRACTION OF CANNABINOID ACIDS

(71) Applicant: Chimera Technology LLC., Palatine, IL (US)

(72) Inventors: Geoffrey A. Bruder, Rocky River, OH (US); Shelby Griebel, Waterloo, IL (US); David Flood, Palatine, IL (US)

(73) Assignee: CHIMERA TECHNOLOGY LLC, Palatine, IL (US)

( * ) Notice: Subject to any disclaimer, the term of this patent is extended or adjusted under 35 U.S.C. 154(b) by 306 days.

(21) Appl. No.: 17/078,387

(22) Filed: Oct. 23, 2020

(65) Prior Publication Data
US 2021/0121794 A1  Apr. 29, 2021

Related U.S. Application Data

(60) Provisional application No. 63/092,567, filed on Oct. 16, 2020, provisional application No. 62/925,820, filed on Oct. 25, 2019.

(51) Int. Cl.
*B01D 11/02* (2006.01)
*C07D 311/80* (2006.01)
(Continued)

(52) U.S. Cl.
CPC ........ *B01D 11/0265* (2013.01); *A61K 36/185* (2013.01); *B01D 11/028* (2013.01);
(Continued)

(58) Field of Classification Search
CPC ............ B01D 11/0288; B01D 11/0292; B01D 11/0211; B01D 11/0257; B01D 11/0265;
(Continued)

(56) References Cited

U.S. PATENT DOCUMENTS 6,061,926 A  5/2000 Paré et al.
8,445,034 B1  5/2013 Coles, Jr.
(Continued)

FOREIGN PATENT DOCUMENTS

CN  106860492 A  6/2017
WO  WO2017057600 A1 * 4/2017  ............. C11B 1/106

OTHER PUBLICATIONS

English Translation of Maeda et al Patent Publication WO2017057600A1, published Apr. 2017. (Year: 2017).*
(Continued)

*Primary Examiner* — Joseph W Drodge
(74) *Attorney, Agent, or Firm* — FLENER IP & BUSINESS LAW; Zareefa B. Flener

(57) ABSTRACT

A method for extracting compounds, including stable natural cannabinoid acids, from plant material, utilizing terpenes as a saturant is described. The invention includes the excitation of the plant material and terpene solvent with microwave, ultrasound, sonication, heat input, and physical agitation or combinations thereof. The invention particularly covers the process as it relates to the extraction of THC-A, CBG-A, and CBD-A and their derivatives from cannabis and hemp for the use in products for medical and recreational use. The combinations of terpene saturant, plant material strain and process variables can be tuned in order to dial in the final resultant product for several variables including but not limited to terpene content, THC-A, CBG-A or CBD-A potency, ratios of THC-A, CBD-A, CBG-A and their derivatives, or flavor profile.

25 Claims, 4 Drawing Sheets

(51) Int. Cl.
  *C07C 51/42* (2006.01)
  *C07C 65/03* (2006.01)
  *A61K 36/18* (2006.01)
  *A61K 36/185* (2006.01)

(52) U.S. Cl.
  CPC ...... *B01D 11/0288* (2013.01); *B01D 11/0292* (2013.01); *C07C 51/42* (2013.01); *C07D 311/80* (2013.01); *C07C 65/03* (2013.01)

(58) Field of Classification Search
  CPC ... B01D 1/00; B01D 3/10; B01D 9/00; B01D 9/0018; B01D 9/0059; B01D 11/0203; B01D 11/0261; B01D 11/028; B01D 15/08; B01D 15/12; B01D 15/125; B01D 36/00; B01D 36/02; B01D 39/06; B01D 39/2055; B01D 39/2058; A61L 2/005; A61L 2/0011; A61L 2/0017; A61L 2/0047; A61L 2/0064; A61L 2/02; A61L 2/022; A61L 2/10; A61L 2/12; A61L 2/202; A61L 2202/21; F26B 5/06; C11B 1/02; C11B 1/025; C11B 1/04; C11B 1/10; C11B 1/104; C11B 1/108; C11B 3/00; C11B 3/001; C11B 3/003; C11B 3/005; C11B 3/006; C11B 3/008; C11B 3/08; C11B 3/12; C11B 3/16; C12N 11/18; A61K 36/00; A61K 36/16; A61K 36/185; A61K 36/268; A61K 36/53; A61K 36/532; A61K 36/62; A61K 36/896; A61K 36/906; A61K 36/9066; C07C 37/004; C07C 39/23; C07C 45/78; C07C 45/79; C07C 45/81; C07C 45/82; C07C 45/85; C07C 49/248; C07C 49/255; C07C 51/42; C07C 65/03; C07C 2601/16; C07C 51/47; C07D 311/80
  USPC ............ 210/634, 638, 748.1, 760, 770, 774; 424/725, 728, 752, 756, 774; 554/8, 20, 554/21, 22, 175, 206; 435/132, 175, 267, 435/271
  See application file for complete search history.

(56) References Cited

U.S. PATENT DOCUMENTS

| | | |
|---|---|---|
| 9,447,198 B2 | 9/2016 | Zhang et al. |
| 10,143,706 B2 | 12/2018 | Kotra et al. |
| 10,272,360 B2 | 4/2019 | Lopa |
| 10,413,845 B1 | 9/2019 | Tegen et al. |
| 10,537,592 B2 | 1/2020 | Kotra et al. |
| 10,745,644 B1 | 8/2020 | Ellis et al. |
| 10,828,341 B2 | 11/2020 | Rivas |
| 10,851,038 B1 | 12/2020 | Novitski et al. |
| 10,941,131 B1 | 3/2021 | Grondin et al. |
| 10,946,308 B2 | 3/2021 | Hari et al. |
| 10,961,174 B2 | 3/2021 | Tegen et al. |
| 10,973,864 B2 | 4/2021 | Venturini Del Greco |
| 11,253,793 B1 | 2/2022 | Thiel et al. |
| 2009/0216007 A1 | 8/2009 | Zhang |
| 2013/0338234 A1 | 12/2013 | Splinter et al. |
| 2017/0008870 A1 | 1/2017 | Dibble |
| 2017/0333505 A1* | 11/2017 | Gharib .................... A23L 29/03 |
| 2018/0344661 A1* | 12/2018 | Finley .................. A61K 31/355 |
| 2019/0282502 A1* | 9/2019 | Boeckl .................. A61K 36/00 |
| 2020/0061136 A1* | 2/2020 | Venturini Del Greco .................... A61K 31/352 |
| 2020/0063061 A1 | 2/2020 | Vanaman |
| 2020/0324501 A1 | 10/2020 | Harrington |
| 2020/0383893 A1 | 12/2020 | Ham et al. |
| 2020/0398180 A1 | 12/2020 | Hospodor |
| 2020/0398184 A1 | 12/2020 | Farokhi et al. |
| 2021/0023155 A1* | 1/2021 | Opperman ......... B01D 11/0288 |
| 2021/0094929 A1 | 4/2021 | Tegen et al. |
| 2021/0100864 A1 | 4/2021 | Ham et al. |
| 2022/0002259 A1* | 1/2022 | Tegen .................. C07D 311/80 |

OTHER PUBLICATIONS

Daniela De Vita et al., "Comparison of Different Methods for the Extraction of Cannabinoids from Cannabis," Natural Product Research, ISSN: 1478-6427, Apr. 29, 2019.

"Terpene Extraction by Ultrasonics," Hielscher Ultrasonics GmbH, https://www.hielscher.com/ultrasonic-terpene-extraction.htm, Aug. 13, 2018.

Notice of References cited (Examiner's Form 892) in co-pending U.S. Appl. No. 17/078,263.

* cited by examiner

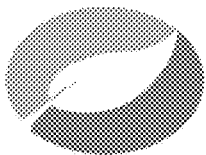

LK Pure Labs

LAB REPORT

Customer: Progressive Treatment Solutions, LLC
Address: 737 Locust St
East St. Louis, IL 62201

Manifest ID: 3737440062657901
Sample: 2019-01-13 Test 37-2
Type: Hydrocarbon Wax
Batch/Lot ID: 8945 3138 5231 4157
Sample ID: 0856 9150 9972 4069

Received: 01/14/2019

Lab ID/Sample Report ID: 20190114PQ
Potency Test Results- WI-001 HPLC-UV

Analysis Date: 01/14/2019

| TEST | WEIGHT % | CONCENTRATION (mg/g) |
|---|---|---|
| CBD | <0.10% | <1.00 |
| CBG | <0.10% | <1.00 |
| CBD-A | <0.10% | <1.00 |
| CBN | <0.10% | <1.00 |
| Delta 9 THC (THC) | <0.10% | <1.00 |
| Delta 8 THC | <0.10% | <1.00 |
| CBC | <0.10% | <1.00 |
| THC-A | 0.42% | 4.20 |
| THC-V | <0.10% | <1.00 |
| TOTAL | 0.42% | 4.20 |

Terpene Test Results- GCMS       Analysis Date: 01/14/2019

| TEST | Microgram Per Gram (ug/g) | TEST | Microgram Per Gram (ug/g) |
|---|---|---|---|
| Alpha-Pinene | 82378.22 | Linalool | N.D. |
| Camphene | N.D. | Fenchyl Alcohol | N.D. |
| Sabinene | N.D. | Borneol | N.D. |
| Beta-Pinene | 4529.76 | Alpha Terpineol (isomer) | N.D. |
| Beta-Myrcene | 481.52 | Gamma Terpineol (isomer) | N.D. |
| Alpha-Phellandrene | N.D. | Beta-Caryophyllene | N.D. |
| Delta-3-Carene | N.D. | Elemene | N.D. |
| Alpha-Terpinene | N.D. | Alpha-Humulene | N.D. |
| P-Cymene | N.D. | Valencene | N.D. |
| Limonene | 885.69 | Cis-Nerolidol | N.D. |
| Eucalyptol | N.D. | Trans Nerolidol | N.D. |
| Ocimene | N.D. | Caryophyllene Oxide | N.D. |
| Gamma-Terpinene | N.D. | Guaiol | N.D. |
| Sabinene Hydrate | N.D. | Alpha-Bisabolol | N.D. |
| Terpinolene | N.D. | | |
| Fenchone | N.D. | Total Terpenes | 88275.19 |

Figure 4

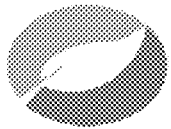

LK Pure Labs

LAB REPORT

Customer: Progressive Treatment Solutions, LLC
Address: 737 Locust St.
East St. Louis, IL 62201

Manifest ID: 3846850615544914
Sample: 2019-10-24 Test 45-1
Type:
Batch/Lot ID:
Sample ID: 9187 3126 8712 6321

Received: 04/02/2020

Lab ID/Sample Report ID: 20200402PW
Potency Test Results - WI-081 HPLC-UV

Analysis Date: 04/08/2020

| ANALYTE | WEIGHT % | CONCENTRATION (mg/g) |
|---|---|---|
| CBD | <0.10% | <1.00 |
| CBG | <0.10% | <1.00 |
| CBD-A | 1.61% | 16.10 |
| CBN | <0.10% | <1.00 |
| Delta 9 THC (THC) | <0.10% | <1.00 |
| Delta 8 THC | <0.10% | <1.00 |
| CBC | <0.10% | <1.00 |
| THC-A | <0.10% | <1.00 |
| THC-V | <0.10% | <1.00 |
| TOTAL | 1.61% | 16.10 |

Terpene Test Results - GCMS

Analysis Date: 04/08/2020

| ANALYTE | CONCENTRATION (ug/g) | ANALYTE | CONCENTRATION (ug/g) |
|---|---|---|---|
| Alpha-Pinene | 9158.28 | Linalool | N.D. |
| Camphene | N.D. | Fenchyl Alcohol | N.D. |
| Sabinene | N.D. | Borneol | N.D. |
| Beta-Pinene | N.D. | Alpha Terpineol (Isomer) | N.D. |
| Beta-Myrcene | 65254.38 | Gamma Terpineol (Isomer) | N.D. |
| Alpha-Phellandrene | 338733.85 | Beta-Caryophyllene | N.D. |
| Delta-3-Carene | N.D. | Elemene | N.D. |
| Alpha-Terpinene | 53142.88 | Alpha-Humulene | N.D. |
| P-Cymene | 438327.71 | Valencene | N.D. |
| Limonene | 48555.88 | Cis-Nerolidol | N.D. |
| Eucalyptol | 11604.79 | Trans Nerolidol | N.D. |
| Ocimene | N.D. | Caryophyllene Oxide | N.D. |
| Gamma-Terpinene | 8913.66 | Guaiol | N.D. |
| Sabinene Hydrate | N.D. | Alpha-Bisabolol | N.D. |
| Terpinolene | 6005.84 | | |
| Fenchone | N.D. | Total Terpenes | 878797.27 |

Figure 5

SOLVENT-LESS EXTRACTION OF CANNABINOID ACIDS

CROSS-REFERENCE TO RELATED APPLICATIONS

This application claims priority to U.S. Provisional Application Ser. No. 62/925,820 filed on Oct. 25, 2019 and U.S. Provisional Application Ser. No. 63/092,567 filed on Oct. 16, 2020, the disclosures of which are hereby incorporated by reference in their entirety.

FIELD OF THE INVENTION

This invention relates to solvent-less extraction of cannabinoid acids from cannabis plants.

BACKGROUND

Extraction of compounds from plant material typically utilizes harsh chemicals which are expensive and can leave residual chemicals within the product for consumers. To remove the desired components from plant-based materials, the plant is often subjected to heat and pressure while submerged in a solvent such as Butane or Ethanol. The solvent is then separated from the useable chemical by a secondary process which uses heat to evaporate the solvent.

Rather than using harsh chemicals to extract the useful plant compounds, for plants natively containing, terpenes, a terpene can be used as the collection media. The plant-based material and, terpene collection media, or "saturant", can be excited or agitated using ultrasound, microwave, heat, pressure, or a combination of these in order to achieve the desired extraction without the use of harsh chemicals. The process of terpene extraction leads to a clean, high purity extraction and, in the case of cannabinoids, is able to perform with near 100% efficiency with the appropriate combination, of terpene and excitation.

Furthermore, cannabinoid acids Cannabidiolic Acid (CBD-A), Cannabigerolic Acid (CBG-A) and Tetrahydrocannabinolic Acid (THC-A) are difficult to extract and maintain in concentration as the acid tail of the compounds is easily destroyed in a process called decarboxylation. Decarboxylation typically affects most, if not all, of the cannabinoid acids within the plant leading to the non-acidic forms of the compounds such as Δ-8-Tetrahydrocannabinol (Δ-8-THC), Δ-9-Tetrahydrocannabinol (Δ-9-THC), Cannabigerol (CBG) and Cannabidiol (CBD). Furthermore, decarboxylation and degradation of cannabinoids into Cannabinol (CBN) or Cannabichromene (CBC) can occur over time in the isolate or distillate due to light or oxygen exposure over time. Due to the difficulty of extracting and storing these compounds containing the chemical acid tail, the only commercially viable forms of the cannabinoid acids are synthetically produced. Synthetically produced cannabinoids have been linked to much more morbidity and mortality than the natural phytocannabinoids.

BRIEF SUMMARY OF THE INVENTION

The subject invention includes the use of terpenes such as, but not limited to, D-Limonene, Myrcene, Phellandrene, Caryophyellene, and Alpha-Pinene for the extraction of cannabinoid acid compounds from plant-based materials, in particular, THC-A and CBD-A from cannabis or hemp. Furthermore, the solvent-less extraction of CBC is addressed. The plant material, including the leaves, stems, and buds can be removed from the plant and immediately processed stored in a freezer or other controlled environment, or dried to remove moisture. Prior to extraction, the plant material may be further chilled to fractionate the plant and break down cell walls, leading the plant to more readily release the desired compounds. Also, the plant material may be soaked in the terpene prior to extraction.

The extraction process may utilize an excitation method, including microwave, ultrasound, sonication, heat input through radiation or conductive elements, or combinations of these methods. The subject invention also covers the use of physical agitation during the extraction process, such as a rotating stir mechanism or forced flow in the saturant. Furthermore, the temperature of the process may be controlled through an external chiller or ice bath of the processing volume. This serves the purpose of allowing the excitation energy to help release the desired compounds while keeping the process temperatures low enough to not degrade the compounds or approach the combustion temperatures of the plant material or saturant.

Vacuum may be used in order to remove oxygen from the process, helping to maintain the integrity of the chemical compounds and reducing the likelihood of combustion by increasing flash temperatures and eliminating the oxidizer for the combustion process. Also, especially in the case of microwave excitation, vacuum allows for a larger pressure differential from inside the plant material to the processing volume which can increase the ability of the process to reclaim desired compounds or reduce the required processing time.

The combinations of terpene saturant, plant material strain and process variables can be tuned in order to dial in the final resultant product for several variables including but not limited to terpene content, THC-A or CBD-A potency, ratios of THC-A or CBD-A and their derivatives, or flavor profile. Particular effects can be achieved through the combinations of these variables leading to products that effect different outcomes on the patient including pain reduction, increased energy and decreased appetite.

BRIEF DESCRIPTION OF THE DRAWINGS

FIG. 4 shows the laboratory results from a solvent-less extraction of live resin flower yielding THC-A as the only cannabinoid.

FIG. 5 shows the laboratory results from the FIG. 3 sample re-tested after 5 months of aging, indicating no degradation in the cannabinoid potency.

DETAILED DESCRIPTION AND BEST MODE OF IMPLEMENTATION

Figure 1:
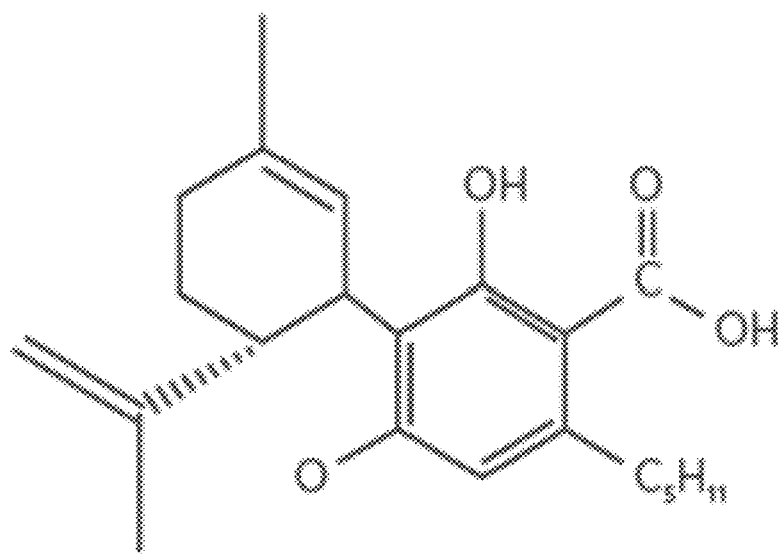
FIG. 1 shows the chemical structure of Cannabidiolic Acid (CBD-A).
Figure 2:
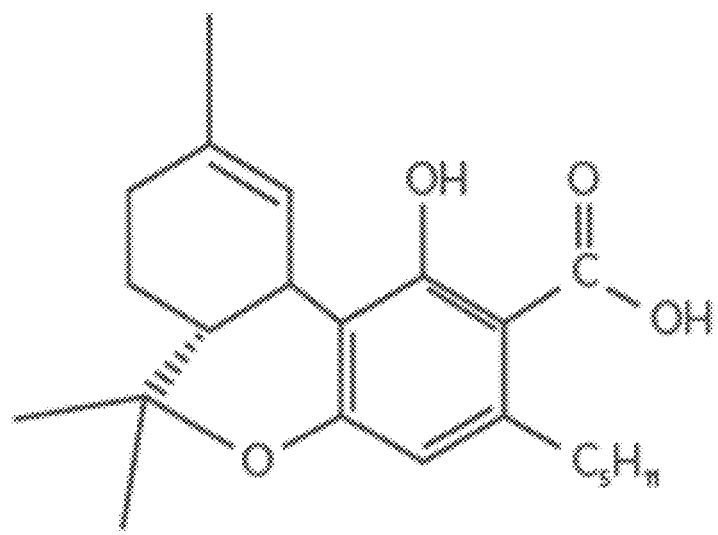
FIG. 2 shows the chemical structure of Tetrahydrocannabinolic Acid (THC-A).
Figure 3:
FIG. 3 shows the laboratory results from a solvent-less extraction of dried flower yielding CBD-A as the only cannabinoid.

According to the first aspect of the invention removal of terpenes, cannabinoids, and/or cannabinoid acids from cannabis flower is conducted using ultrasonic excitation within at least one terpene as the saturant and an external excitation.

According to the second aspect of the invention removal of terpenes, cannabinoids, and/or cannabinoid acids from cannabis flower is conducted using microwave excitation within at least one terpene as the saturant.

According to the third aspect of the invention the plant material is stored in a sub-zero freezer and soaked in the saturant for up to 12 hours prior to extraction.

According to the fourth aspect of the invention the ratio of saturant to plant material is 0.02-1.0 g/L.

According to the fifth aspect of the invention a temperature of <30° C. is maintained throughout the extraction process.

According to the sixth aspect, of the invention the plant material is dried prior to extraction to remove moisture content.

According to the seventh aspect of the invention the plant material is cured prior to extraction to allow for internal terpene evolution and reduction in moisture content.

According to the eighth aspect of the invention removal of terpenes, cannabinoids, and/or cannabinoid acids from cannabis flower is conducted using microwave and ultrasonic excitation within a terpene or plurality of terpenes as the saturant, specifically Alpha-Pinene.

We claim:

1. A process for extraction of cannabinoid acids from cannabis flower plant material, wherein said cannabinoid acids are selected from the group consisting of cannabigerolic acid, cannabidiolic acid and tetrahydrocannabinolic acid, the process comprising the step of using ultrasonic excitation in a process chamber in conjunction with at least one terpene as a saturant, wherein the ratio of plant material to a total amount of the at least one terpene used as the saturant is 0.02-1.0 g/L.

2. The process of claim 1 wherein the plant material is stored in a sub-zero freezer and soaked in the saturant for up to 12 hours prior to introduction of the plant material to the process chamber.

3. The process of claim 1 wherein a temperature of <30° C. is maintained in the process chamber throughout the process by the use of an external chiller.

4. The process of claim 1 wherein the plant material is dried prior to introduction of the plant material to the process chamber to remove moisture content.

5. The process of claim 1 wherein the plant material is cured prior to introduction of the plant material to the process chamber.

6. The process of claim 1 wherein a vacuum is pulled on the process chamber.

7. The process of claim 1 wherein the process chamber is pressurized with an inert gas.

8. The process of claim 1 wherein the process chamber is pressurized with a vaporized terpene.

9. The process of claim 1 wherein the at least one terpene is Alpha-Pinene.

10. A process for extraction of cannabinoid acids from cannabis flower plant material, wherein said cannabinoid acids are selected from the group consisting of cannabigerolic acid, cannabidiolic acid and tetrahydrocannabinolic acid the process comprising the step of using microwave excitation in a process chamber in conjunction with a terpene or plurality of terpenes as a saturant, wherein the ratio of plant material to a total amount of the terpene or the plurality of terpenes used as the saturant is 0.02-1.0 g/L.

11. The process of claim 10 wherein the plant material is stored in a sub-zero freezer and soaked in the saturant for up to 12 hours prior to introduction of the plant material to the process chamber.

12. The process of claim 10 wherein a temperature of <30° C. is maintained in the process chamber throughout the process by the use of an external chiller.

13. The process of claim 10 wherein the plant at is dried prior to introduction of the plant material to the process chamber to remove moisture content.

14. The process of claim 10 wherein the plant material is cured prior to introduction of the plant material to the process chamber.

15. The process of claim 10 wherein a vacuum is pulled on the process chamber.

16. The process of claim 10 wherein the process chamber is pressurized with an inert gas.

17. The process of claim 10 wherein the process chamber is pressurized with a vaporized terpene.

18. A process for extraction of cannabinoid acids from cannabis flower plant material, wherein said cannabinoid acids are selected from the group consisting of cannabigerolic acid, cannabidiolic acid and tetrahydrocannabinolic acid, the process comprising the step of using microwave and ultrasonic excitation in a process chamber in conjunction with a terpene or plurality of terpenes as a saturant, wherein the ratio of plant material to a total amount of the terpene or the plurality of terpenes used as the saturant is 0.02-1.0 g/L.

19. The process of claim 18 wherein the plant material is stored in a sub-zero freezer and soaked in the saturant for up to 12 hours prior to introduction of the plant material to the process chamber.

20. The process of claim 18 wherein a temperature of <30° C. is maintained in the process chamber throughout the process by the use of an external chiller.

21. The process of claim 18 wherein the plant material is dried prior to introduction of the plant material to the process chamber to remove moisture content.

22. The process of claim 18 wherein the plant material is cured prior to introduction of the plant material to the process chamber.

23. The process of claim 18 wherein a vacuum is pulled on the process chamber.

24. The process of claim 18 wherein the process chamber is pressurized with an inert gas.

25. The process of claim 18 wherein the process chamber is pressurized with a vaporized terpene.

* * * * *